United States Patent
Wei et al.

(10) Patent No.: US 9,681,733 B2
(45) Date of Patent: *Jun. 20, 2017

(54) COSMETIC LIQUID EXTRACTOR COMPRISING NONIONIC POLYMERS

(71) Applicant: Avon Products, Inc., Suffern, NY (US)

(72) Inventors: Xiaolan Wei, Mahwah, NJ (US);
Santiago Uribe, Butler, NJ (US);
Desiree Mazich, Sparta, NJ (US);
Eileen A. Higgins, Secaucus, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,211

(22) Filed: Jan. 29, 2014

(65) Prior Publication Data

US 2014/0161505 A1   Jun. 12, 2014

Related U.S. Application Data

(63) Continuation of application No. 13/222,370, filed on Aug. 31, 2011, now Pat. No. 8,673,279.

(51) Int. Cl.
*A61Q 19/00* (2006.01)
*A45D 40/26* (2006.01)
*A61K 8/368* (2006.01)
*A61K 8/81* (2006.01)

(52) U.S. Cl.
CPC .............. *A45D 40/26* (2013.01); *A61K 8/368* (2013.01); *A61K 8/8129* (2013.01); *A61K 8/8176* (2013.01); *A61Q 19/00* (2013.01)

(58) Field of Classification Search
None
See application file for complete search history.

(56) References Cited

U.S. PATENT DOCUMENTS

| | | |
|---|---|---|
| 5,512,277 A | 4/1996 | Uemura et al. |
| 5,985,299 A | 11/1999 | Buerger et al. |
| 6,042,844 A | 3/2000 | Ishida et al. |
| 6,159,493 A | 12/2000 | Chen et al. |
| 6,174,536 B1 | 1/2001 | Crotty |
| 6,190,683 B1 | 2/2001 | Hoshi et al. |
| 6,221,382 B1 | 4/2001 | Ishida et al. |
| 6,299,605 B1 | 10/2001 | Ishida |
| 6,306,882 B1 | 10/2001 | Irie et al. |
| 6,444,215 B1 | 9/2002 | Pinna et al. |
| 6,649,181 B1 | 11/2003 | Miner |
| 6,942,869 B2 | 9/2005 | Osumi et al. |
| 7,168,878 B2 | 1/2007 | Tani |
| 8,673,279 B2 * | 3/2014 | Wei ............... A61K 8/368 424/401 |
| 2002/0197291 A1 | 12/2002 | Ulbricht et al. |
| 2003/0175333 A1 | 9/2003 | Shefer et al. |
| 2004/0146555 A1 | 7/2004 | Ulbricht et al. |
| 2005/0276842 A1 | 12/2005 | Zhang et al. |
| 2006/0236470 A1 * | 10/2006 | Sabnis et al. ............... 8/405 |

FOREIGN PATENT DOCUMENTS

| | | | |
|---|---|---|---|
| EP | 1266840 | * | 12/2002 |
| EP | 1417956 | * | 5/2004 |

* cited by examiner

*Primary Examiner* — Jyothsna Venkat
(74) *Attorney, Agent, or Firm* — Brian P. McCloskey

(57) ABSTRACT

Aqueous liquid compositions are provided, which comprise nonionic polymers, such as polyvinyl alcohol (PVA), polyvinylpyrrolidone (PVP), or combinations thereof, and which are free of or substantially free of salt-forming groups. The aqueous liquids form solid, flexible films after direct application to skin, and the films may be peeled from the skin to remove adhered keratotic plugs from pores of the skin. The compositions are easily applied to skin, without dripping, with fingers, a brush, or other applicators.

9 Claims, No Drawings

COSMETIC LIQUID EXTRACTOR COMPRISING NONIONIC POLYMERS

CROSS-REFERENCE TO RELATED APPLICATIONS

This patent application is a continuation of, and claims priority to, U.S. patent application Ser. No. 13/222,370, filed on Aug. 31, 2011. The entirety of the aforementioned application is incorporated herein in its entirety by reference.

FIELD OF THE INVENTION

The present invention relates generally to methods and compositions for removing keratotic plugs from pores of human skin. More specifically, the present invention relates to aqueous liquid compositions comprising nonionic polymers and optionally skin active ingredients, which form solid films after application to the skin. The films may be peeled from the skin to remove adhered keratotic plugs from pores of the skin.

BACKGROUND OF THE INVENTION

Keratotic plugs, such as blackheads or open comedones, are known to form in the pores of human skin from the keratinization of dead epidermal cells combined with dust and sebaceous secretions. Such keratotic plugs are commonly found on the face and are generally considered to be aesthetically displeasing. Unfortunately, facial cleansers and makeup removers, which do not use physical pulling force to remove keratotic plugs, are not well-suited to eliminate such skin ailments.

Deep cleansing pore strips with adhesive on one side and a backing on the other are known. Although these strips allow for the removal of keratotic plugs by peeling the strip from the skin, their fixed size and shape make it difficult for many consumers to apply the strips to certain areas of the face. For example, the presence of a backing layer may make it difficult for a consumer to apply the strip to the side or crease of the nose. Moreover, the adhesive layer sometimes detaches from the backing when peeled from the skin, which decreases the effectiveness of the product.

U.S. Pat. No. 5,512,277, incorporated by reference herein in its entirety, discloses direct application of liquid compositions to remove keratotic plugs. The compositions disclosed therein comprise a resin functionalized with salt-forming groups. Upon application to the skin, the resin is allowed to dry to a film, which is then removed along with any keratotic plugs that adhere to the resin. Although such compositions are theoretically more convenient than the above mentioned pore strips, they unfortunately suffer from low viscosities due at least in-part to the inclusion of salt-forming groups. The compositions may therefore drip during application, making them difficult to apply to particular areas of the skin. The patent teaches that "pack preparations, which are applied to the skin and peeled off after dried, and which generally contain a nonionic polymer such as polyvinyl alcohol and polyvinyl pyrrolidone as a major component of a film forming agent, are still not sufficiently effective for removing dirt from the skin pores and especially for removing keratotic plugs."

U.S. Pat. No. 6,159,493, incorporated by reference herein in its entirety, discloses an acne extraction patch coated with a polymer solution comprising 0.5% to 5% polyvinyl alcohol, 1% to 20% polyvinyl pyrrolidone, and an excipient. The polymer solution is applied to the acne patch, which is moistened with water and applied to the face or nose. The polymer solution is not applied directly to the skin in the absence of the acne patch.

The foregoing discussion is presented solely to provide a better understanding of the nature of the problem confronting the art and should not be construed in any way as an admission as to prior art nor should the citation of any reference herein be construed as an admission that such reference constitutes "prior art" to the instant application.

SUMMARY OF THE INVENTION

It has surprisingly been found that aqueous liquid compositions comprising nonionic polymers, such as polyvinyl alcohol (PVA), polyvinylpyrrolidone (PVP), or combinations thereof, which are free of or substantially free of salt-forming groups, may be employed to remove keratotic plugs from pores of human skin. Such compositions are easily applied to skin, without dripping, with fingers, a brush, or other applicators. When allowed to dry to a flexible, solid film, the nonionic polymers adhere to keratotic plugs such that the plugs may be removed from the pores by peeling away the film from the skin.

In one aspect a method for removing keratotic plugs from pores of human skin is provided. In a first step of the method, an aqueous liquid is applied to skin suffering from keratotic plugs. The aqueous liquid includes from about 10% to about 20% by weight PVA and from about 5% to about 15% by weight PVP. The aqueous liquid is substantially free of polymers containing salt-forming groups and has a viscosity of from about 25,000 cps to about 200,000 cps. Once the aqueous liquid is applied, water and optional volatile solvents are allowed to evaporate such that a flexible, solid film is formed on the surface of the skin. The film is adherent to keratotic plugs in the pores of the skin. In order to remove the keratotic plugs, the film is peeled from the skin such that keratotic plugs adherent thereto are removed from the pores.

In another aspect, an aqueous liquid composition for removing a keratotic plug from skin is provided. The aqueous liquid includes from about 10% to about 20% by weight PVA, from about 5% to about 15% by weight PVP, and from about 65% to about 85% by weight water. The aqueous liquid is substantially free of polymers containing salt-forming groups and has a viscosity from about 25,000 cps to about 200,000 cps. The liquid optimally comprises one or more skin actives, such as anti-acne agents (e.g., salicylic acid), antioxidants, alpha-hydroxy acids, and the like.

In yet another aspect of the invention, a product for removal of keratotic plugs from human skin is provided. The product includes a container having a flexible body defining an interior space with an amount of an aqueous liquid disposed within the interior space. The container includes a neck to reversibly engage a sealing cap and an orifice in the neck through which the aqueous liquid is dispensed when the body of the container is squeezed. The cap prevents the aqueous liquid from being dispensed while the cap is attached to the body and may engage with the neck of the container by means of complementary threading or the like. The aqueous liquid may be any of the keratotic removing compositions descried herein.

These and other aspects of the invention will be better understood by reading the following detailed description and appended claims.

DETAILED DESCRIPTION

All terms used herein are intended to have their ordinary meaning in the art unless otherwise provided. All concentrations are in terms of percentage by weight of the specified component relative to the entire weight of the keratotic plug removing composition. Unless otherwise defined, the phrase "substantially free" refers to an amount of a component that is sufficiently low such that the component contributes no significant properties to the bulk and, in any event, will be less than 0.5% by weight and preferably less than 0.1% by weight. As used herein, "consisting essentially of" means that the composition or component may include additional ingredients, but only if the additional ingredients do not materially alter the basic and novel characteristics of the claimed compositions or methods.

The invention generally provides keratotic removing compositions suitable for use on human skin, including skin of the forehead, nose, chin, and other parts of the face and body. In its broadest implementation, the invention is directed to aqueous liquid compositions comprising one or more nonionic polymers. The nonionic polymers may be either water soluble or water dispersible, but are preferably water soluble. The nonionic polymer may be suitably selected from the group consisting of PVA, polyvinyl acetate, PVP, polyester, cellulose, cellulose derivatives (e.g., ethers and esters), other polysaccharides, gelatin, collagen, and mixtures thereof.

In preferred embodiments, the keratotic plug removing compositions comprise PVA. The amount of PVA present in the compositions will typically range from more than 10% by weight to about 20% by weight, but may be higher or lower depending on the desired viscosity and peel strength. The amount of PVA may be, without limitation, 11%, 12%, 13%, 14%, 15%, 16%, 17%, 18%, 19% or 20% by weight. In one embodiment, the keratotic plug removing composition may comprise from about 12.5% to about 17.5% PVA by weight. It has been found that compositions comprising greater than about 10% by weight PVA are easy to apply to the skin without dripping and form films having sufficient peel strength to remove keratotic plugs.

The PVA component of the composition may comprise a single PVA material or may comprise two or more PVA materials. In one embodiment, a low viscosity PVA and a high viscosity PVA are incorporated into a keratotic plug removing composition. As used herein, the term "low viscosity PVA" refers to a PVA material having a viscosity of from about 1.0 cps to about 20 cps, preferably from about 3.0 cps to about 10 cps, and more preferably from about 5.2 cps to about 6.2 cps. One suitable low viscosity PVA is sold under the name CELVOL 205 by Celenese Corp. Further, the term "high viscosity PVA," as used herein, refers to a PVA material having a viscosity greater than 20 cps and up to about 100 cps, more specifically from about 25 cps to about 75 cps, and even more specifically from about 40 cps to about 60 cps. A suitable high viscosity PVA is CELVOL 540 from Celenese Corp., which has a viscosity of from about 45 cps to about 55 cps. All PVA viscosities described herein are determined in a 4% aqueous solution at 20° C.

When the composition comprises both a low viscosity PVA and a high viscosity PVA, the low viscosity PVA is typically present in a weight ratio to the high viscosity PVA of between about 5:1 to about 1:5, more typically from about 4:1 to about 1:4, preferably from about 3:1 to about 1:3, more preferably from about 2:1 to about 1:2, and more preferred still from about 3:2 to about 2:3; including an embodiment of about 1:1.

The PVA employed in the present invention may be derived from polyvinyl acetate by hydrolysis. For example, the high and/or low viscosity PVA will typically be from about 80% to about 100% hydrolyzed, more typically from about 85% to about 95% hydrolyzed. The CELVOL products are said to have a degree of hydrolysis from about 87% to about 89%. PVA material with a higher degree of hydrolysis will exhibit greater adhesion and peel strength than those with lower degrees of hydrolysis. They are also expected to contribute to a higher viscosity.

The keratotic plug removing compositions preferably also comprise an amount of PVP. The compositions will typically comprise PVP in an amount of from about 5% to about 15% by weight, and preferably from about 7.5% to about 12.5% by weight.

The PVP employed in the instant invention will typically have an average molecular weight from about 8,000 Daltons to about 4,000,000 Daltons. In certain preferred embodiments, the PVP will have an average molecular weight from about 60,000 Daltons to about 3,000,000 Daltons, or from about 400,000 Daltons to about 2,000,000 Daltons. A suitable PVP material is PVP K-90 by ISP Corp, which has an average molecular weight of about 1,300,000 Daltons. The PVP is believed to contribute to film forming ability and flexibility to the relevant film.

The most preferred embodiments of the keratotic plug removing composition of the instant invention comprise both PVA and PVP. The PVA and PVP may be present in the composition in any weight ratio, but generally will be present in a PVA to PVP weight ratio of from about 4:1 to 1:4; 3:1 to 1:3; 2:1 to 1:2; 3:2 to 2:3; or 1:1. In a currently preferred formulation, the ratio of PVA to PVP is between about 2.5:1 to about 3:1.

In one variant according to the invention, PVA-PVP copolymers may be employed together with, or in place of, the individual PVA and PVP compounds. PVA-PVP copolymers will suitably have a molecular weight high enough to allow the composition to be peeled from the skin without tearing, but low enough to allow for adequate adhesion to skin and solubility in water. Accordingly, the PVA-PVP copolymers will typically, but not necessarily, have an average molecular weight of from about 10,000 to about 5,000,000 Daltons, more specifically from about 50,000 to about 3,00,000 Daltons. The PVA-PVP copolymers may comprise any form, such as but not limited to a block copolymer, graft copolymer or random copolymer.

U.S. Pat. No. 5,512,277, incorporated by reference herein in its entirety, discloses resins functionalized with salt-forming groups. However, it has been found that when such salt-forming groups are included in the keratotic plug removing composition, the product's viscosity becomes too low for direct paint-on application to prevent the occurrence of dripping during application. Moreover, it has been found that the presence of salt-forming groups in the keratotic plug removing compositions result in unstable formulations when PVA is employed.

Accordingly, in preferred embodiments, the polymers are free from or substantially free from salt-forming groups including those described in U.S. Pat. No. 5,512,277, incorporated by reference herein. Such salt-forming groups include but are not limited to one or more of the group consisting of carboxyl groups, sulfonic acid groups, sulfuric acid residual groups (—$OSO_3H$), phosphoric acid residual groups (—$OPO_3H_2$), nitric acid residual groups (—$NO_2$), amino groups, ammonium groups, and the like. The inventive keratotic plug removing compositions are preferably free of polymethacryloyloxyethyltrimethylammonium chloride. Without these salt-forming groups, it is believed that the compositions are capable of maintaining acceptable stability when stored for three months at about 45° C.

The nonionic polymers used herein may be either dissolved or dispersed in a volatile solvent, which may be any solvent so far as it can stably dissolve or disperse the nonionic polymers therein, provided that it is safe (i.e., non-toxic) for topical application to human skin. For example, the solvent may comprise water, ethanol, isopropanol or combinations thereof. Although the amount and type of solvent may depend on the desired properties of the keratotic plug removing composition, the composition will typically comprise from about 50% to about 85% by weight water and, preferably, from about 60% to about 80% by weight water. In other one variant, the composition comprises from about 65% to about 75% by weight water.

The keratotic plug removing compositions may comprise a second volatile solvent in addition to water. The second solvent may be, without limitation, a lower alcohol (e.g., a $C_1$-$C_5$ alcohol) such as ethanol, isopropanol, and mixtures thereof. Moreover, the co-solvent, if present, will typically be present in the composition in an amount from about 0.1% to about 10% by weight; more typically from about 0.5% to about 7.5% by weight or about 5% by weight.

In any event, the total amount of solvent used should result in a composition having a viscosity ranging from about 10,000 cps to about 250,000 cps, preferably from about 25,000 cps to about 200,000 cps, more preferably from about 25,000 cps to about 100,000 cps, and most preferably from about 25,000 cps to about 50,000 cps. Of course, in addition to the amount of solvent used, the viscosity will depend on the particular nonionic polymers employed and any additional additives (e.g., viscosity adjusters) included in the composition.

The compositions may further comprise any number of customary additives. For example, the compositions may comprise one or more skin benefiting agents selected from the group consisting of salicylic acid; alpha hydroxyl acids, such as but not limited to glycolic acid and lactic acid; thiodipropionic acid; amino acids; peptides and botanical extracts to name a few. In one preferred embodiment, the composition comprises salicylic acid, which helps to prevent acne and blackheads from forming. The one or more skin benefiting agents may be present in the composition in an amount from about 0.001% to about 5% by weight, preferably from about 0.01% to about 2.5%, and more preferably from about 0.1% to about 2% by weight.

The keratotic plug removing compositions may further comprise one or more plasticizing agents to enhance the film properties. One type of plasticizing agent is polyhydric alcohols, such as but not limited to ethylene glycol, diethylene glycol, triethylene glycol, and higher polyethylene glycols; propylene glycol and polypropylene glycols; butylene glycols; glycerol and polyglycerols; sugar alcohols such as sorbitol and xylitol; adducts of glycerols with ethylene oxide; and combinations or variations thereof. The one or more plasticizing agents may comprise hydrocarbons such as liquid paraffin, solid paraffin, squalane, etc.; higher fatty acids such as oleic acid and isostearic acid; high alcohols such as lauryl alcohol; natural oils such as jojoba oil, olive oil, egg yolk oil, castor oil, and palm oil; synthetic oils such as poly(dimethylsioxane); nonionic surfactants such as fatty acid esters of glycerin; sorbitan fatty acid esters, polyoxyethylene sorbiatan fatty acid esters, polyoxyethylene castor oil, polyoxyethylene hardended castor oil, polyoxyethylene alkyl ether, and combinations thereof. The one or more plasticizing agents may be present in the composition in an amount from about 0.001% to about 5% by weight, preferably from about 0.01% to about 2.5%, and more preferably from about 0.1% to about 1% by weight.

Because the inventive pore-cleansing formulations are applied in the wet state, the formulation must be allowed to dry on the skin before being pulled away to remove debris and/or keratotic plugs. If a user removes the film before it is sufficiently dry, the product adhesion to skin may be sub-optimal, with only limited pulling power. However, it may be difficult for a user to determine the appropriate amount of time to allow for drying. Accordingly, in certain embodiments, the keratotic plug removing composition comprises an opacifying agent and/or a coloring agent (e.g., pigment, lake, or dye) to provide a visual cue to a user to indicate when the drying time is complete. In this embodiment, the composition may change color or opacity as it dries on the skin. For example, the formulation may contain a dye and/or an opacifying agent so that the composition appears whitish when it is initially applied to skin, but becomes more transparent and/or colored as it dries.

The opacifying agent is not particularly limited, as long as the clear or transparent appearance of the composition is reduced. Exemplary opacifying agents include, but are not limited to, PVP-styrene copolymers, glycol distearate, ethylene glycol monostearate, guanine, and combinations thereof. The opacifying agents may be present in the composition in an amount from about 0.1% to about 5%, preferably from about 0.5% to about 2%, and most preferably from about 1% to about 2%.

In some embodiments, the keratotic plug removing composition may further comprise a thickening agent which is preferably a non-ion polymer such as but not limited to carrageenan, pectin, xanthan gum, pullulan, hydroxyethylcellulose, hydroxypropylcellulose, or pectin. Further, the compositions may comprise other additives including but not limited to antioxidants, bacteriocides, humectants, preservatives, fragrances, moisturizing agents, pH adjusting agents, and/or combinations thereof. Such additives may be included in any amount, as long as they do not impair the composition's ability to remove keratotic plugs and do not cause excessive irritation when the composition is applied to skin.

The compositions described herein are applied to the skin while in an aqueous liquid state. Upon application, the composition flows into the pores of the skin, including those pores having keratotic plugs. The composition is then allowed to dry for a period of time, for example, from about 5 to about 45, preferably 10 to 30, most preferably 10 to 20 minutes, sufficient to allow a solid film to develop. Of course, the drying time will depend on the amount (i.e., thickness) of the composition applied to the skin. Once dried, the films may be peeled from the skin without the use of a pack or sheet-like backing layer.

During the drying time, an amount of water and/or any optional solvents included in the composition are allowed to evaporate, causing the composition to harden into a peelable, flexible, solid film. Such film forms on the surface of the skin and is adherent to keratotic plugs contained within pores of the skin. The films of the invention, when dried, should have a sufficient peel strength such that the film can be readily lifted from the skin in tact, without causing discomfort to the user, but while still having sufficient adhesion with the keratotic plugs to remove the plugs from the pores upon peeling.

In one embodiment of the invention, the composition is provided in a container comprising a flexible body. The flexible body of the container defines an interior space which may be filled with the aqueous keratotic plug removing composition. The body of the container will comprise an orifice, through which the composition is dispersed when the body is squeezed. The orifice may be in communication with a tip such that the tip may be pressed against the skin during application of the composition to aid in spreading a film over the skin surface. In certain embodiments, the container may further comprise a cap which is removably attached to the flexible body by complimentary threads or the like such that the composition is prevented from being dispensed while the cap is attached to the body. When the cap is not attached to the body, the composition may be dispensed through the orifice by squeezing the body. The product or associated packaging or labeling may include instructions directing the user to apply the composition to skin affected by blackheads, allow the dry film to develop, and peel the film from the skin to remove blackheads.

In other embodiments, the composition can be applied to the skin using a brush-type applicator, a roller-ball-type applicator, or the like. In still other embodiments, the composition can be applied to the skin from a container having a rigid body and comprising a pump and/or elevator evacuation mechanism.

EXAMPLE I

A keratotic plug removing composition according to the invention is provided in Table 1.

TABLE 1

| Phase | Material | Amount |
|---|---|---|
| A | Water | q.s. |
| A | Preservative | 0.2% |
| B | PVA (Low Viscosity) | 10% |
| B | PVA (High Viscosity) | 5% |
| B | PVP | 10% |
| C | Ammonium Hydroxide | 0.28% |
| D | Preservative | 0.1% |
| D | Water | 1% |
| E | Ethanol Alcohol | 5% |
| E | Salicylic Acid | 0.5% |
| E | Opacifier | 0-5% |
| E | Dye | 0-0.1% |
| E | Fragrance | 0.1% |

In a first step, the materials of Phase A were mixed together at a temperature of about 20° C. The Phase B ingredients were then added to the Phase A materials, and the entire contents were mixed to homogeneity at a temperature of between about 85° C. to about 91° C. The batch was than cooled to a temperature of between about 71° C. and about 74° C. and the Phase C materials were added. The Phase D materials were first mixed in a separate mixing apparatus before being added to the batch. The batch was then cooled to about 60° C., and the Phase E materials were separately mixed before being added thereto. Finally, the batch was cooled to a temperature of between about 32° C. and about 35° C. and mixed.

The keratotic plug removing composition was tested on ten consumers and was found to be easy to apply and easy to peel from the skin, without discomfort. Importantly, the composition was found to be efficacious in removing keratotic plugs, oil, and other skin debris from skin on and around the nose.

The composition was also tested to determine stability over a four week period for a number of different storage conditions. The composition was stable in storage conditions of 5° C., 20° C., 40° C., and 50° C. It was also stable through three freeze/thaw cycles as well as through cycling between 5° C. and 40° C.

EXAMPLE II

The following Example shows that, as the total PVA polymer is increased above 10% by weight, keratotic plug removing efficiency of the composition unexpectedly increases.

As shown in Table 2, a keratotic plug removing composition according to the invention (Inventive Composition) was prepared comprising 10% by weight low viscosity PVA, 5% by weight high viscosity PVA, and 10% by weight PVP. The low viscosity PVA to high viscosity PVA weight ratio of the Inventive Composition was 2:1.

Comparative Example A was prepared having the same amount of PVP (10%) and the same weight ratio of low viscosity PVA to high viscosity PVA (2:1) as the Inventive Composition. However, the total PVA present in Comparative Example A was only 10% by weight, as compared to the 15% of the Inventive Composition.

Comparative Example B was also prepared with a 2:1 weight ratio of low viscosity PVA to high viscosity PVA and 10% by weight total PVA. However, Example B differs from both the Inventive Composition and Comparative Example A in that it includes 15% PVP by weight.

TABLE 2

| Material | Trade Name | Inventive Composition (w.t. %) | Comparative Example A (w.t. %) | Comparative Example B (w.t. %) |
|---|---|---|---|---|
| PVA (LV) | CELVOL 205[1] | 10 | 6.7 | 6.7 |
| PVA (HV) | VINOL 540[2] | 5 | 3.3 | 3.3 |
| PVP | PVP K-90[3] | 10 | 10 | 15 |

[1]Low Viscosity PVA by Celanese;
[2]High Viscosity PVA by Air Prod. and Chem.;
[3]by ISP The viscosity of each sample was tested, and each sample was applied to skin to determine application properties, drying time, and removal properties. The results are shown in Table 3.

TABLE 3

| | Viscosity (cps) | Application | Drying Time (min) | Removal |
|---|---|---|---|---|
| Inventive Composition | 30,200 | Easy to Apply; Formed Continuous Film | 20 | Peeled as Entire Film; Removed Keratotic Plugs |
| Comparative Example A | 2,700 | Dripping; Difficult to Form Continuous Film | 20 | Thin Film Could Not Be Peeled; Keratotic Plugs Were Not Removed |
| Comparative Example B | 21,300 | Easy to Apply; Formed Continuous Film | 35 | Brittle Film Broke Into Pieces When Peeled |

As shown, the Inventive Composition had a viscosity between about 25,000 cps and about 35,000 cps, which allowed for the easy application of the product to the skin without dripping. The Inventive Composition formed a continuous, comfortable layer on the skin and dried after about 20 minutes. Importantly, the dried film was flexible and solid, and remained intact when peeled from the skin, with adequate peel strength to remove keratotic plugs.

In contrast, Comparative Example A was characterized by a low viscosity which provided for a product that was difficult to apply to the skin due to dripping and failure to form a continuous film. Moreover, upon drying, the film could not be peeled and failed to remove keratotic plugs.

Although Comparative Example B had a higher viscosity than Example A due to the larger amount of PVP, the product was characterized by a very long drying time and broke into pieces when peeled from the skin.

EXAMPLE III

The following Example illustrates the effects of ionic polymers in the formulations. As shown in Table 4, two formulations were prepared: (1) a formula without salt-forming groups on the polymer, according to the invention, and (2) a formula comprising 30% by weight of a methyl-vinyl ether and maleic acid polymer (Gantrez® S97BF by ISP).

TABLE 4

| Material | Formulation Without Salt-Forming Groups (w.t. %) | Formulation Including Salt-Forming Groups (w.t. %) |
| --- | --- | --- |
| Water | q.s. | q.s. |
| Methylparaben | 0.2% | 0.2% |
| PVA | 20% | 20% |
| Disodium EDTA | 0.1% | 0.1% |
| Gantrez ® S97BF Solution | 0% | 30% |

Both formulations were stored for one week at temperatures of from about 40° C. to about 50° C. and the viscosities were determined. Surprisingly, the formulation without the salt-forming groups maintained a near constant viscosity throughout the storage period. However, the formulation with the salt-forming groups showed a rapid increase in viscosity and formed a thick, heavy gel during storage that was not suitable for application to the skin.

The invention having been described by the forgoing description of the preferred embodiment, it will be understood that the skilled artisan may make modifications and variations of these embodiments without departing from the spirit or scope of the invention as set forth in the following claims.

All patent and non-patent literature discussed above is hereby incorporated by reference in its entirety for all purposes.

We claim:

1. An aqueous liquid composition for removing a keratotic plug comprising from more than 10% to about 20% by weight polyvinyl alcohol (PVA), wherein said PVA comprises a low viscosity PVA having a viscosity from about 1.0 to 20 cps and a high viscosity PVA having a viscosity higher than the viscosity of said low viscosity PVA, said high viscosity PVA having a viscosity from about 20 to about 100 cps said viscosities as determined in a 4% aqueous solution at 20° C.; wherein said PVA is derived from hydrolysis of polyvinyl acetate and has a degree of hydrolysis from about 85% to about 95%; from about 5% to about 15% by weight polyvinylpyrrolidone (PVP), said composition being substantially free of salt-forming groups, and having a viscosity from about 25,000 cps to about 200,000 cps.

2. The aqueous liquid composition according to claim 1 further comprising one or more skin benefiting agents selected from the group consisting of salicylic acid, glycolic acid, thiodipropionic acid, amino acids, peptides, botanical extracts, and mixtures thereof.

3. The aqueous liquid composition according to claim 2, wherein the one or more skin benefiting agents comprises salicylic acid.

4. The aqueous liquid composition according to claim 1 comprising from about 12.5% to about 17.5% PVA by weight and from about 7.5% to about 12.5% PVP by weight.

5. The aqueous liquid composition according to claim 1, further comprising from about 0.1% to about 10% by weight of an ethanol co-solvent.

6. A product for removal of keratotic plugs from human skin comprising a container comprising a flexible body defining an interior space having an amount of an aqueous liquid disposed therein, said body comprising an aperture adapted to dispense said aqueous liquid when the body is squeezed, the container further comprising a cap removably attached to said flexible body such that said aqueous liquid is prevented from being dispensed while said cap is attached to said body, wherein said aqueous liquid comprises from more than 10% to about 20% by weight polyvinyl alcohol (PVA), wherein said PVA comprises a low viscosity PVA having a viscosity from about 1.0 to 20 cps and a high viscosity PVA having a viscosity higher than the viscosity of said low viscosity PVA, said high viscosity PVA having a viscosity from about 20 to about 100 cps said viscosities as determined in a 4% aqueous solution at 20° C.; wherein said PVA is derived from hydrolysis of polyvinyl acetate and has a degree of hydrolysis from about 85% to about 95%; from about 5% to about 15% by weight polyvinylpyrrolidone (PVP), and about 65% to about 85% by weight water, said aqueous liquid being substantially free of salt-forming groups, and having a viscosity from about 25,000 cps to about 200,000 cps.

7. The product according to claim 6, wherein said aqueous liquid further comprises salicylic acid.

8. The product according to claim 6, wherein said aqueous liquid comprises from about 12.5% to about 17.5% PVA by weight and from about 7.5% to about 12.5% PVP by weight.

9. The product according to claim 6, wherein said aqueous liquid further comprises from about 0.1% to about 10% ethanol by weight.

* * * * *